INVENTORS.
JOHN R. ANDERSON
GEORGE S. SOMEKH
BY James A. Barlow
ATTORNEY

INVENTORS.
JOHN R. ANDERSON
GEORGE S. SOMEKH
BY
ATTORNEY

United States Patent Office

Re. 27,494
Reissued Sept. 26, 1972

27,494

SEPARATION OF AROMATIC HYDROCARBONS FROM NONAROMATIC HYDROCARBONS

John R. Anderson, Mount Kisco, and George S. Somekh, New Rochelle, N.Y., by Union Carbide Corp., assignee Original No. 3,492,365, dated Jan. 27, 1970, Ser. No. 553,336, May 27, 1966. Application for reissue Feb. 26, 1971, Ser. No. 119,063
Int. Cl. C07c *7/10, 7/02, 7/00*
U.S. Cl. 260—674 SE 10 Claims

Matter enclosed in heavy brackets [ ] appears in the original patent but forms no part of this reissue specification; matter printed in italics indicates the additions made by reissue.

ABSTRACT OF THE DISCLOSURE

Aromatic hydrocarbons are separated from a mixture containing the same together with nonaromatic hydrocarbons. The mixture is first contacted with a solvent which selectively dissolves the aromatic fraction and the extract from this step which contains the aromatic hydrocarbon dissolved in the solvent is subjected to a secondary extraction step using a solvent which has a higher boiling point than and is non-azeotropic with the original feed mixture. Thereafter the aromatic hydrocarbons are recovered by a series of distillation steps.

Figure 1:
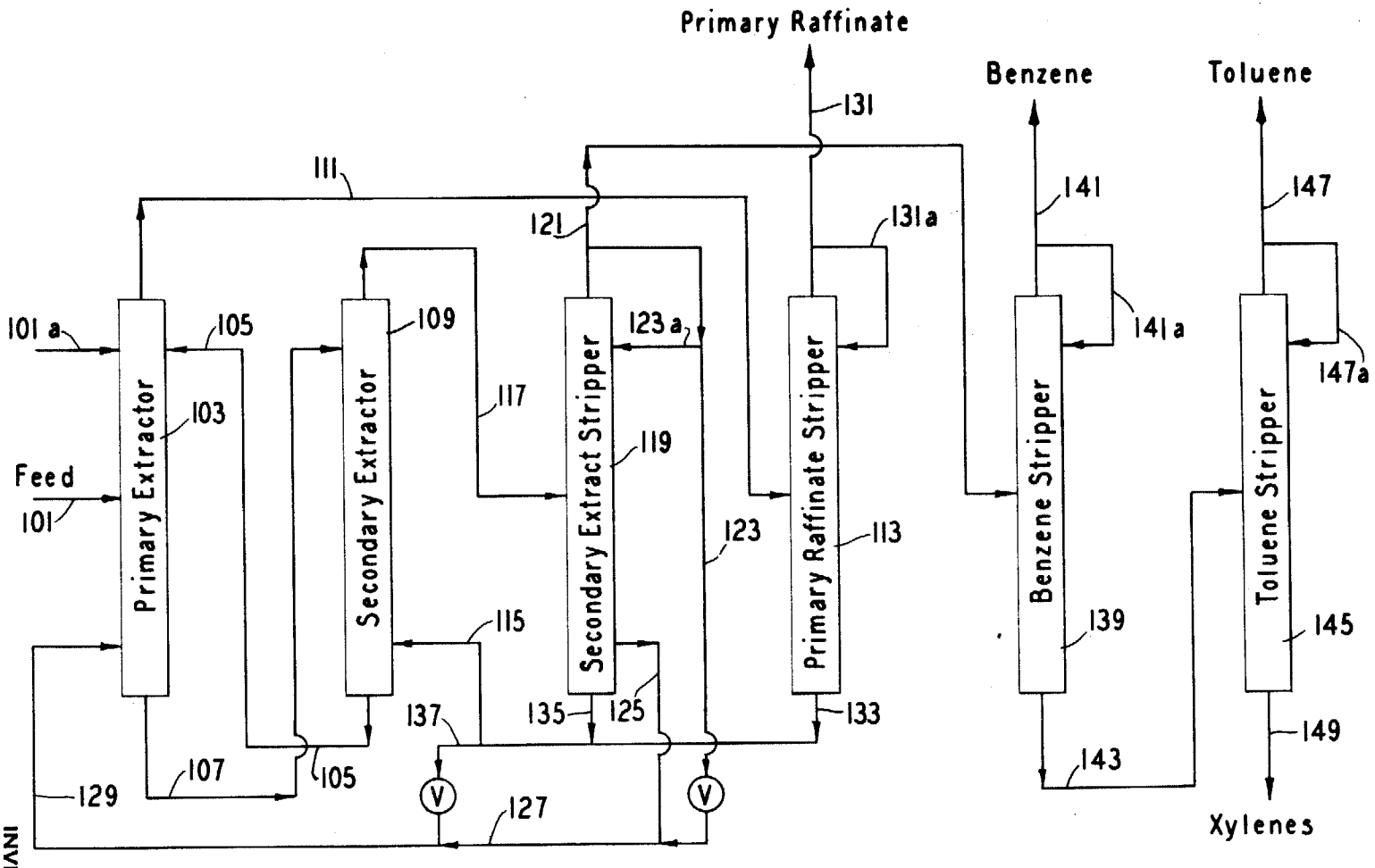

This invention relates to a process for the separation of aromatic hydrocarbons from mixed hydrocarbon feedstocks containing the same together with nonaromatic hydrocarbons. It is particularly related to a process for separating benzene, toluene and xylenes from feed mixtures containing these aromatic hydrocarbons together with nonaromatic hydrocarbons and is more particularly concerned with the production of benzene in high purity.

It is well known to separate aromatic hydrocarbons such as benzene, toluene and xylenes from hydrocarbon mixtures containing the same. According to known methods an aromatic-containing feed is introduced into a solvent extraction zone wherein it is countercurrently contacted with an extraction solvent such as ethylene glycol, diethylene glycol, propylene glycol, dipropylene glycol, or other higher molecular weight glycols and polyglycols. An extract phase is removed from the bottom of the extraction zone consisting of the aromatics dissolved in the extraction solvent. A raffinate phase essentially nonaromatic in character is removed overhead. This raffinate is washed with water to remove any entrained extraction solvent therefrom, and the nonaromatic hydrocarbons are recovered as overhead product. The extract phase is subjected to distillative operation, in a distillation column, using live steam to strip the aromatics from the solvent. The aromatics and the steam are removed overhead, condensed and separated into a water layer and an aromatic layer. The water is removed, reheated to steam, if desired, and reused in the process. Part of the aromatics is refluxed to the distillation zone or the extraction zone, whereas the remainder can be removed as product. In many cases the extraction solvent which is withdrawn from the bottom of the distillation zone contains some water which may have to be removed prior to recycling of the solvent to the extraction zone.

The solvent extraction process just described has several limitations. The capacity of the extraction solvent for absorption of aromatic hydrocarbons is usually poor due to the presence of water in the extraction solvent. This reduced capacity necessitates the use of large quantities of extraction solvent for efficient and quantitative extraction of the aromatics from nonaromatic hydrocarbons. Consequently the equipment required to handle such large quantities of extraction solvent is necessarily large and expensive. When low boiling extraction solvents are used, both the solvent and the water contained therein have high latent heats of vaporization. Consequently, the removal of water from the solvent becomes an expensive operation due to the necessity of application of large quantities of heat in the distillation operation. On the other hand, when high boiling solvents are used, in addition to large heat requirements, high distillation temperatures are necessary for efficient removal of water from the extraction solvent. The application of such high temperatures may result in thermal and/or oxidative degradation of the solvent, particularly in the presence of air. This, of course, reduces the efficiency of operation. Furthermore, the extraction solvents heretofore employed very often boil at or near the boiling points of the aromatic hydrocarbons which must be separated. This necessitates complicated and expensive distillation and recovery methods and apparatus for recovery of the extraction solvent. These prior art processes also include water washing of the hydrocarbon products and therefore require subsequent distillation of the water from the hydrocarbons.

It has now been discovered that benzene in high purity and toluene and xylenes in relatively high purity can be separated from their admixture with nonaromatic hydrocarbons in accordance with the process of this invention in a manner which would obviate the difficulties heretofore inherent in most of the prior art processes for the recovery of these materials. Furthermore, it is possible by the practice of this invention to recover benzene in high purity of the order of about 99.99% or even 100%. In addition, toluene and xylenes can also be recovered in relatively high purities of the order of about 95% or even higher. The term xylenes as employed throughout the present application has reference to the various forms of xylenes, i.e., ortho, meta and para xylenes and to ethylbenzene.

Figure 2:
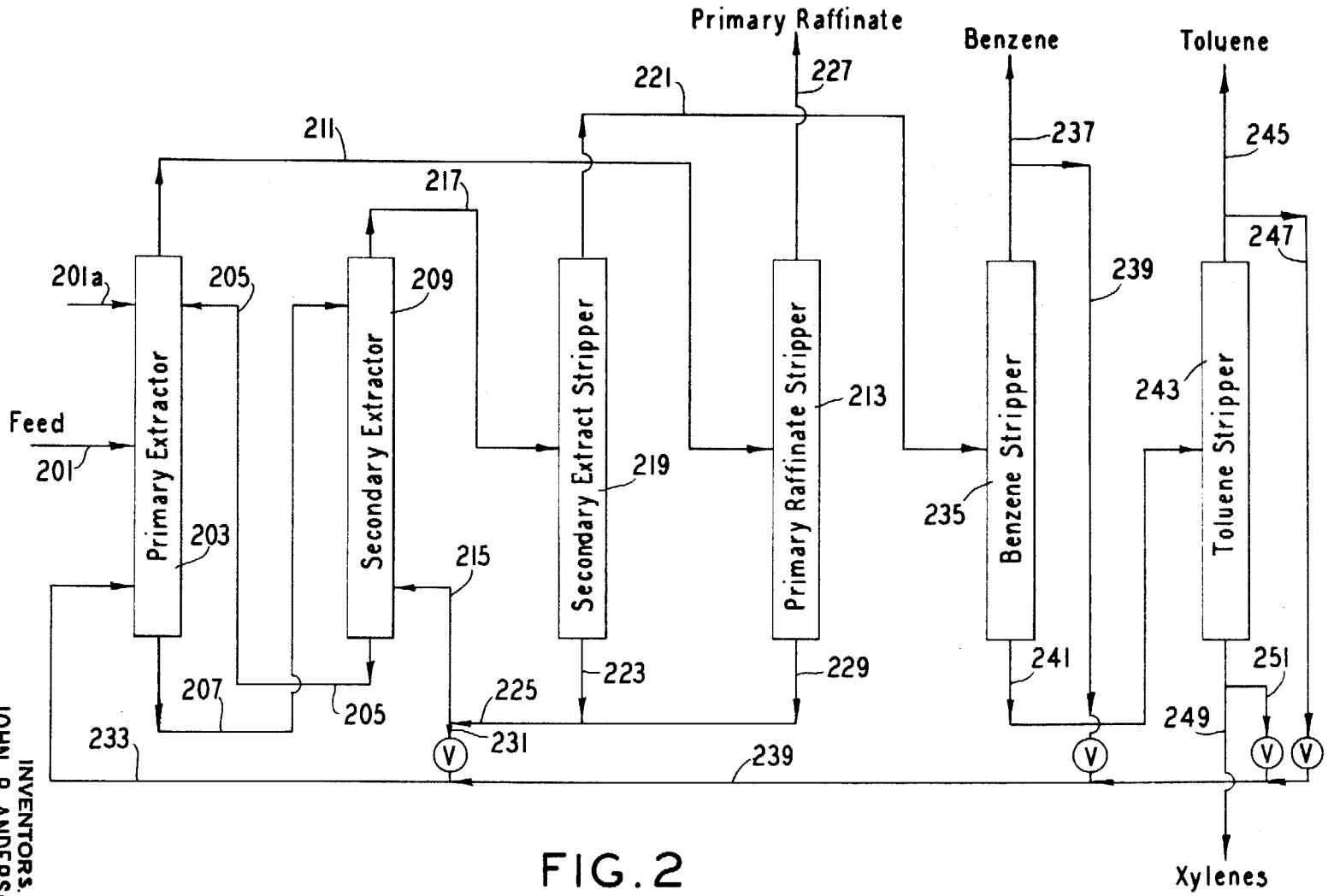

The process of this invention in its broadest aspect contemplates contacting a mixed hydrocarbon feedstock containing benzene, toluene and xylenes in an extraction zone hereinafter referred to as primary extractor with a solvent capable of selectively dissolving the aromatic fraction of the feed only, which solvent will hereinafter be referred to as the primary solvent and described in further detail. The extract from the primary extractor (hereafter referred to as primary extract) consisting of the aromatics dissolved in the primary solvent is further extracted in a secondary extractor with a second solvent hereinafter referred to as the secondary solvent, which solvent must have a higher boiling point than and be non-azeotropic with the feed to the primary extractor and which solvent is a straight chain or branched chain paraffinic, or naphthenic hydrocarbon to be further described hereinafter. The overhead from the secondary extractor (hereinafter called secondary extract) is then distilled to remove an overhead which consists essentially of benzene, toluene and xylenes which is then subjected to additional distillative operations to remove high purity benzene as the overhead in a benzene stripping column and toluene and xylenes, respectively, as the overhead and bottoms stream in a toluene stripping column. In addition to the specific requirements with respect to the nature of the secondary solvent it has been further found that the provision of a recycle to the primary extraction column forms a significant part of this invention. Thus as it is shown in FIGURE 1 it has been found that the provision of a recycle stream to the primary extractor which is withdrawn at a point below the feed point in the secondary extract stripper will further contribute to the high purity benzene as well as the toluene and xylenes which are recoverable by the process of this invention. It should be emphasized that this recycle stream is extremely low in benzene impurities. A similar recycle stream is shown in FIGURE 2 having the same characteristics as the recycle stream described above which is basically the extremely low benzene impurities in the recycle stream and which therefore results in the production of high purity benzene from this process.

Another significant feature of this invention is the low ratio of this recycle-to-feed to the primary extractor. Whereas in most of the prior art processes this recycle ratio is as high as about 1.2:1 and is generally about 1:1, the process of this invention requires low recycle ratio which ranges from about 0.05:1 to about 0.5:1 and is preferably from about 0.1:1 to about 0.3:1. This recycle ratio is based on the volume of the recycle per volume of feed to the primary extractor.

The primary solvents which are generally employed for the extraction of the aromatic fraction of the hydrocarbon feed in the primary extractor are water-free, water-soluble selective solvents which have higher boiling points than and are non-azeotropic with the hydrocarbon feed to the primary extractor. Exemplary solvents of this type are the lower polyalkylene glycols, for example, dipropylene glycol, tripropylene glycol, dibutylene glycol, tributylene glycol, and higher molecular weight water-soluble glycols of this series, or mixtures thereof. The selectivity of these solvents for the absorption of aromatics can be improved by the addition to the solvent of so-called antisolvents. When antisolvents such as ethylene glycol, diethylene glycol, and higher molecular weight glycols of this series, propylene glycol, butylene glycol, or any mixture of such glycols are used in conjunction with the primary solvents, the selectivity of the primary solvent for the absorption of aromatic hydrocarbons is effectively increased. The choice of solvents and antisolvents is generally dependent upon the composition of the feed to the primary extractor, the degree of separation required, and other operating variables which are involved.

Under certain conditions the antisolvents may be used in lieu of the primary solvents in the primary extraction step.

Other solvents can be used as primary solvents among which are "Cellosolve" solvents such as alkyl ethers of ethylene glycol, for example, methyl "Cellosolve," ethyl "Cellosolve," propyl "Cellosolve," and butyl "Cellosolve"; "Carbitol" solvents such as alkyl ethers of diethylene glycol, for example, methyl "Carbitol," ethyl "Carbitol," propyl "Carbitol," butyl "Carbitol," sulfolane, N-methyl pyrrolidone, etc.

The secondary solvents which are suitable for the practice of this invention are paraffinic and naphthenic hydrocarbons which are higher boiling than and are non-azeotropic with the feed to the primary extractor, and which contain a maximum of about 1% aromatic hydrocarbons and preferably no more than about 0.5% aromatic hydrocarbons. This secondary solvent can be either a straight chain or branched chain paraffinic hydrocarbon, naphthenic hydrocarbon or mixtures of both hydrocarbons. Exemplary secondary solvents are n-decane, n-dodecane, 2-methyl decane, 2,2-dimethyl decane, n-hexyl cyclohexane, 2-methyl hexyl cyclohexane, etc.

The invention will be more clearly understood by referring to the following detailed description taken in connection with the drawings attached hereto and made a part of this application. In all of the drawings the feedstock is a mixture of aromatic and nonaromatic hydrocarbons wherein the aromatic hydrocarbons consist of benzene, toluene and xylenes.

FIGURE 1 in the drawings is a schematic flow representation of one illustrative embodiment of the present invention.

FIGURE 2 is a schematic flow representation of another illustrative embodiment of this invention.

In FIGURE 1 the feed is introduced via line 101 into a primary extractor 103 wherein it is contacted with the primary solvent which is introduced into the primary extractor through line 105. The nonaromatic fraction of the feed ascends through the primary extractor 103 wherefrom it is removed as primary raffinate through line 11. The primary raffinate which contains small amounts of primary and secondary solvents is introduced into a primary raffinate stripper 113. The primary extract which consists essentially of the aromatic fraction of the feed and the primary solvent is introduced through line 107 into a secondary extractor 109 wherein it is countercurrently contacted with a secondary solvent which is introduced into the secondary extractor through line 115.

Initially the primary solvent is introduced to the primary extractor via line 101d and after the operation of both extractors has attained equilibrium conditions the feed of the primary solvent through line 101d is discontinued and the principal source of the primary solvent will be the bottoms from the secondary extractor. Similarly, the secondary solvent can first be introduced into the secondary extractor from an outside source (not shown) until the process achieves steady state conditions. Thereafter the principal source of the secondary solvent is from the process itself.

In this embodiment as well as in the other embodiment shown in FIGURE 2, the extractors and the strippers are generally of the type which are in common industrial use and require no elaboration. They may be either packed or equipped with the appropriate trays to facilitate the extraction and the distillation operations.

The primary extractor can be operated at a temperature of from about ambient to about 175° C., preferably from about 50° C. to about 125° C., a pressure of from about 15 p.s.i.a. to about 200 p.s.i.a., preferably from about 30 p.s.i.a. to about 100 p.s.i.a., and at a solvent-to-feed volume ratio of from about 1:1 to about 10:1, preferably from about 2:1 to about 6:1.

The secondary extractor can be operated at a temperature and pressure essentially similar to the conditions in the primary extractor. However, the solvent-to-feed ratio in the secondary extractor is from about 0.1:1 to about 5:1, preferably from about 0.2:1 to about 2:1.

The overhead from the secondary extractor which consists essentially of secondary solvent together with the aromatic hydrocarbons and small amounts of primary solvent is withdrawn via line 117 and introduced into a secondary extract stripper 119 wherein an overhead fraction is removed through line 121 consisting essentially of benzene, toluene and xylenes. A portion of this overhead stream may be returned to the primary extractor via line 123 which after joining a side stream withdrawn through line 125 at a point below the feed entry into the secondary extract stripper may be returned to the primary extractor via lines 127 and 129.

In the raffinate stripper the nonaromatic fraction of the feed is withdrawn overhead through line 131 and the bottoms which consist essentially of the secondary solvent and a small amount of primary solvent is withdrawn through line 133 and is returned to the secondary extractor via line 115 after joining the bottoms from the secondary extract stripper which is withdrawn through line 135. A portion of the combined flow through lines 133 and 135 may be returned to the primary extractor through line 137 which joins line 129 prior to entering the primary extractor.

The secondary extract stripper overhead which consists essentially of benzene, toluene and xylenes is introduced through line 121 into benzene stripper 139 wherein high purity benzene is removed overhead through line 141. The bottoms from the benzene stripper consisting essentially of toluene and xylenes are introduced via line 143 into a toluene stripper 145 wherein high purity toluene is removed overhead through line 147 and bottoms product consisting essentially of xylenes is withdrawn through line 149.

The secondary extract stripped can be operated at a temperature of from about 80° C. to about 250° C. and at subatmospheric, atmospheric or superatmospheric pressure. Similarly, the primary raffinate stripper can be operated at from about 65° C. to about 250° C. and at subatmospheric, atmospheric or superatmospheric pressure. Both the secondary extract stripper and the primary raffinate stripper are advantageously operated at atmospheric pressure.

In the embodiment of the invention illustrated in FIGURE 1, all strippers are operated under reflux conditions. Thus lines 123a, 131a, 141a and 147a represent the reflux to the secondary extract stripper 119, primary raffinate stripper 113, benzene stripper 139 and toluene stripper 145, respectively.

Referring now to FIGURE 2 the feed is introduced via line 201 to a primary extractor 203 wherein it is countercurrently contacted with the primary solvent which enters the primary extractor through line 205. The various streams in this figure contain the same constituents as their corresponding streams in FIGURE 1. Similarly, all strippers are operated under reflux (not shown for simplicity).

A primary extract is withdrawn from the bottom of the primary extractor through line 207 and it is introduced into a secondary extractor 209. The nonaromatic fraction of the feed ascends through the primary extractor wherefrom it is removed as a primary raffinate through line 211 and it is introduced into a primary raffinate stripper 213.

In the secondary extractor 209 the primary extract is contacted with a secondary solvent which is introduced into the secondary extractor through line 215. The secondary solvent ascends through secondary extractor 209 wherein it is countercurrently contacted with the descending primary extract. The secondary solvent strips the aromatics from the primary extract and a secondary extract leaves the secondary extractor 209 through line 217. The secondary raffinate is withdrawn from the secondary extractor and is recycled throughl ine 205 to the primary extractor. In actual operation the primary solvent is initially introduced into the primary extractor through line 201a until the operation of the primary and the secondary extractors achieve equilibrium conditions after which the principal source of the primary solvent will be the secondary raffinate. Similarly, the secondary solvent is first introduced into the secondary extractor from an external source (not shown) as indicated in connection with FIGURE 1.

The secondary extract which consist essentially of the aromatic hydrocarbons and the secondary solvent is introduced into a secondary extract stripper 219 wherein the aromatics are removed overhead by distillation through line 221. This overhead consists essentially of benzene, toluene and xylenes. The bottoms from the secondary extract stripper is withdrawn through line 223 and is recycled to the secondary extractor via line 225 and 215. The primary raffinate is subjected to distillative operation in the primary raffinate stripper 213 wherein the primary raffinate is withdrawn overhead via line 227. The bottoms from the primary raffinate stripper 213 is withdrawn via line 229 and is recycled together with the bottoms from the secondary extract stripper to secondary extractor 209. Part of the combined recycle is introduced into the lower section of the primary extractor 203 through lines 231 and 233.

The secondary extract stripper overhead which is withdrawn via line 221 is introduced into a benzene stripper 235 wherein high purity benzene is removed overhead via line 237. Part of the overhead benzene may be returned to the primary extractor 203 through lines 239 and 233. The bottoms from the benzene stripper which consist essentially of toluene and xylenes is withdrawn via line 241 and introduced into a toluene stripper 243 wherein the toluene is removed overhead via line 245. A portion of the toluene may be returned to the primary extractor 203 via line 247. The bottoms from the toluene stripper is withdrawn via line 249 and consist essentially of xylenes. A portion of this bottoms product may be returned to the primary extractor via line 251 which joins the material flowing through lines 247, 239 and 231 and enters the primary extractor via line 233.

The conditions which are maintained in the various columns in this embodiment of the invention are essentially the same as the corresponding conditions described in connection with description of the embodiment illustrated by FIGURE 1.

While the present invention has heretofore been described with certain degree of particularity, it should be understood, of course, that numerous modifications and revisions are suggested by this description which nevertheless fall within the purview and scope of this invention. The novelty and success of the process of this invention are largely predicted upon the selection of the primary solvent, the seconary sovent and the recycle to the primary extraction zone. Other variables are ascertainable by those skilled in the art after judicious selection of the critical variables and determination of the degree of purity of benzene as well as the degrees of purity of toluene and xylenes which are desired.

The following examples will further illustrate the process of this invention. The feed in all examples was a mixture of hydrocarbons having the following compositions:

| | Volume percent |
|---|---|
| Benzene | 11 |
| Toluene | 18 |
| Xylenes | 12 |
| Cyclohexane | 3 |
| Methyl cyclohexane | 2 |
| Methyl cyclopentane | 2.5 |
| 2,2,4-trimethyl pentane | 2.5 |
| n-Heptane | 46 |
| Trimethyl pentanes (2,2,3-, 2,3,4- and 2,3,3-) | 2 |
| n-Nonane | 1 |
| Total | 100.0 |

EXAMPLE 1

This example illustrates substantially that embodiment of the invention which is described in FIGURE 1.

The feed was introduced into an extraction column (primary extraction). This column was of the multistage reciprocating type and contained a plurality of perforated plates centrally mounted on a vertical shaft driven by a motor in an oscillatory manner. Dry triethylene glycol was introduced at the top plate of this column and the feed was introdced at the midsection. A reflux having the following composition was fed to the bottom of this column.

| | Volume percent |
|---|---|
| Secondary solvent | 39.9 |
| Benzene | 9.0 |
| Toluene | 21.0 |
| Xylenes | 30.0 |

This reflux corresponds to the reflux which can be obtained from the secondary extract stripper (line 125, FIGURE 1) adjusted with secondary solvent flowing through line 137 and aromatic hydrocarbons flowing through line 123, all as shown in FIGURE 1. The secondary solvent was normal paraffinic hydrocarbons boiling in the range of 175° C. to 248° C. The extraction operation was carried out at the following conditions:

| | | |
|---|---|---|
| Temperature | ° C. | 80 |
| Solvent/feed | (vol./vol.) | 6.05/1 |
| Reflux/feed | (vol./vol.) | 0.36/1 |
| Agitator speed setting | | 450 |

The primary extract which was obtained from this extraction operation consisted of the following:

| | Volume percent |
|---|---|
| Benzene | 4.8 |
| Toluene | 6.5 |
| Xylenes | 6.6 |
| Secondary solvent | 1.2 |
| Triethylene glycol | 80.9 |

There were no detectable impurities in this extract. The impurities herein refer to all feed components other than benzene, toluene and xylenes. The absence of impurities in this extract stream indicates that high purity benzene, toluene and xylenes can be obtained by subsequent distillation of the extract.

The procedure outlined above was repeated except that the agitator setting was lowered to 375 (lower agitator setting indicates lower agitator speed and vice versa). The primary extract which was obtained had the following composition:

| | Volume percent |
|---|---|
| Benzene | 9.0 |
| Toluene | 3.0 |
| Xylenes | 2.0 |
| Cyclohexane | <.1 |
| n-Heptane | <.1 |
| Methylene cyclopentane | <.1 |
| Secondary solvent | 1.0 |
| Triethylene glycol | 85.0 |

The presence of impurities in this extract was due to the lowered agitator setting.

The latter extract was subjected to a second extraction step (secondary extraction) employing the same extractor which was previously described. The secondary solvent was introduced at the bottom of the extraction column which was operated at 60° C. and a 1:1 solvent-to-feed volume ratio. Triethylene glycol free of hydrocarbon feed was obtained as the bottoms product and secondary extract was obtained as the overhead. This secondary extract was distilled at one atmosphere pressure in a batch still using a column 1½ inches in diameter and 4 feet long packed with ¼ inch glass helices. The distillate which was recovered in three fractions had the following purities:

| | Volume percent |
|---|---|
| Benzene | 99 |
| Toluene | 99+ |
| Xylenes | 99.0 |

Essentially all the aromatic hydrocarbons were stripped from the secondary solvent which was recovered at bottoms.

This example indicated that high purity benzene, toluene and xylenes can be recovered by the process of this invention. The experimental procedure was carried out in a step-wise manner due to convenience of laboratory facilities. However, the invention is just as operable when carried out in a continuous manner.

EXAMPLE 2

This example illustrates substantially that embodiment of the invention which is described in FIGURE 2.

The feed was subjected to primary extraction in a manner essentially similar to that described in Example 1 except that the agitator setting was 400 and the reflux consisted of 39.9 volume percent secondary solvent and 60.1 volume percent benzene, respectively. This reflux corresponds to that which can be obtained in the process described in FIGURE 2 from lines 231 and 239. The primary extract which was obtained had the following composition:

| | Volume percent |
|---|---|
| Benzene | 15.6 |
| Toluene | 2.5 |

| | Volume percent |
|---|---|
| Xylenes | 0.9 |
| Secondary solvent | 1.0 |
| Triethylene glycol | 80.9 |

Once again it is noted that there are no detectable impurities in this extract which indicates that high purity benzene, toluene and xylenes can be recovered by subsequent distillation.

The above operation was repeated except that the agitator setting was increased to 425 and the plate spacings were somewhat varied. The extract which was obtained in this operation had the following composition:

| | Volume percent |
|---|---|
| Benzene | 8.5 |
| Toluene | 6.0 |
| Xylenes | 3.0 |
| Cyclohexane | <.1 |
| Methyl cyclopentane | <.1 |
| 2,2,4-trimethyl pentane | <.1 |
| Secondary solvent | 0.5 |
| Triethylene glycol | 81.7 |

The presence of impurities in this extract is, of course, due to the changed conditions. This primary extract was fed to the top of a secondary extraction column which was the same as the column described in Example 1. This column was operated essentially in the same manner as the secondary extraction column in Example 1 and triethylene glycol essentially free from hydrocarbon feed was obtained as the bottoms product. The secondary extract was removed as overhead and was distilled at one atmosphere pressure in the distillation column such as that described in Example 1. The distillate which was recovered in three fractions had the following purities:

| | Volume percent |
|---|---|
| Benzene | 99 |
| Toluene | 99.9 |
| Xylenes | 97.4 |

What is claimed is:

[1. A process for separating aromatic hydrocarbons from mixed hydrocarbon feedstock containing the same comprising the following steps:

(a) contacting said feedstock with a primary solvent in a primary extraction zone at a temperature of about ambient temperature to about 175° C. and a pressure of about 15 p.s.i.a. to about 200 p.s.i.a., said primary solvent being a water-soluble organic solvent having a higher boiling point than and being non-azeotropic with the feedstock;

(b) withdrawing from the primary extraction zone a primary solvent-aromatic hydrocarbons phase and an essentially non-aromatic hydrocarbons phase as primary extract and primary raffinate, respectively;

(c) contacting said primary extract with a secondary solvent in a secondary extraction zone at a temperature and pressure essentially similar to the conditions in the primary extraction zone wherein said secondary solvent is selected from the group consisting of paraffinic and naphthenic hydrocarbons having higher boiling points than and being non-azeotropic with the feedstock to the primary extraction zone;

(d) withdrawing a secondary extract consisting essentially of secondary solvent, aromatic hydrocarbons, and primary solvent from the secondary extraction zone and subjecting same to distillation to recover aromatic hydrocarbons;

(e) subjecting the primary raffinate to distillation;

(f) recycling to the primary extraction zone primary solvent and secondary solvent from the distillations of secondary extract and primary raffinate.]

2. The process defined in claim 1 wherein the recycle includes a portion of the aromatic hydrocarbons from the distillation of the secondary extract.

3. The process defined in claim 1 wherein the *extracting* solvent-to-feed ratio, by volume, in the primary extraction zone is about 1:1 to about 10:1 and the *extracting* solvent-to-primary extract ratio, by volume, in the secondary extraction zone is about 0.1:1 to about 5:1.

4. The process defined in claim 2 wherein the *extracting* solvent-to-feedstock ratio, by volume, in the primary extraction zone is about 1:1 to about 10:1 and the *extracting* solvent-to-primary extract ratio, by volume, in the secondary extraction zone is about 0.1:1 to about 5:1.

5. The process defined in claim 1 wherein the primary solvent is a polyalkylene glycol.

6. The process defined in claim 3 wherein the primary solvent is a polyalkylene glycol.

7. The process defined in claim 1 wherein the primary solvent is selected from the group consisting of triethylene glycol, sulfolane, and N-methyl pyrrolidone.

8. The process defined in claim 3 wherein the primary solvent is selected from the group consisting of triethylene glycol, sufolane, and N-methyl pyrrolidone.

9. The process defined in claim 7 wherein the secondary solvent is n-undecane.

10. The process defined in claim 8 wherein the secondary solvent is n-undecane.

*11. A process for separating aromatic hydrocarbons from mixed hydrocarbon feedstock containing the same using a primary solvent which is a water-soluble organic solvent having a higher boiling point than and being non-azeotropic with the feedstock and a secondary solvent selected from the group consisting of paraffinic and naphthenic hydrocarbons having higher boiling points than and being non-azeotropic with the feedstock comprising the following steps:*

*(a) contacting said feedstock with primary solvent as the extracting solvent and secondary solvent as reflux in a primary extraction zone at a temperature of about ambient temperature to about 175° C. and a pressure of about 15 p.s.i.a to about 200 p.s.i.a;*

*(b) withdrawing from the primary extraction zone a primary solvent-aromatic hydrocarbons phase as primary extract and an essentially non-aromatic hydrocarbons phase comprising aliphatic hydrocarbons, secondary solvent, and a small amount of primary solvent as primary raffinate;*

*(c) contacting said primary extract with secondary solvent as the extracting solvent in a secondary extraction zone at a temperature and pressure essentially similar to the conditions in the primary extraction zone;*

*(d) withdrawing a secondary extract consisting essentially of secondary solvent, aromatic hydrocarbons, and a small amount of primary solvent a secondary raffinate comprising primary solvent from the secondary extraction zone;*

*(e) subjecting the secondary extract to distillation to recover aromatic hydrocarbons;*

*(f) recycling the secondary raffinate to the primary extraction zone;*

*(g) subjecting the primary raffinate to distillation;*

*(h) recycling to the primary extraction zone primary solvent and secondary solvent from the distillation of the primary raffinate; and*

*(i) recycling to the secondary extraction zone secondary solvent from the distillation of the secondary extract.*

References Cited

The following references, cited by the Examiner, are of record in the patented file of this patent or the original patent.

UNITED STATES PATENTS

| | | | |
|---|---|---|---|
| 2,243,873 | 6/1941 | Lyman | 208—313 |
| 2,378,808 | 6/1945 | Sweeney | 208—313 |
| 2,618,591 | 11/1952 | Anderson | 203—68 |
| 2,727,848 | 12/1955 | Georgian | 260—674 |
| 2,826,619 | 3/1958 | Powers et al. | 260—674 |
| 3,186,937 | 6/1965 | Anderson et al. | 208—314 |

FOREIGN PATENTS

| | | | |
|---|---|---|---|
| 829,432 | 3/1960 | Great Britain | 260—674 |

DELBERT E. GANTZ, Primary Examiner

C. E. SPRESSER, Jr., Assistant Examiner

U.S. Cl. X.R.

208—314, 321; 203—44, 46, 68

PO-1050
(5/69)

UNITED STATES PATENT OFFICE
CERTIFICATE OF CORRECTION

Patent No. Re. 27,494 Dated September 26, 1972

Inventor(s) J. R. Anderson and G. S. Somekh

It is certified that error appears in the above-identified patent and that said Letters Patent are hereby corrected as shown below:

Rewrite claim 2 to read as follows:

2. The process defined in claim 1 wherein [the recycle includes] a portion of the aromatic hydrocarbons from the distillation of the secondary extract is recycled to the primary extraction zone.

At column 10, line 8, after "solvent", insert --and--.

Signed and sealed this 29th day of May 1973.

(SEAL)
Attest:

EDWARD M.FLETCHER,JR.
Attesting Officer

ROBERT GOTTSCHALK
Commissioner of Patents